US012708402B2

(12) United States Patent
Eisenthal et al.

(10) Patent No.: US 12,708,402 B2
(45) Date of Patent: Aug. 18, 2026

(54) TROCAR AND STYLET STABILIZER

(71) Applicant: The Johns Hopkins University, Baltimore, MD (US)

(72) Inventors: Andrew Eisenthal, Brooklyn, NY (US); Clifford R. Weiss, Baltimore, MD (US); Shashwat Gupta, Baltimore, MD (US); Wade Schutte, Centennial, CO (US); Robert Patrick Liddell, Lutherville, MD (US); Edward Ruppel, III, Saratoga, CA (US); Sabrina Liu, Cambridge, MA (US)

(73) Assignee: The Johns Hopkins University, Baltimore, MD (US)

(*) Notice: Subject to any disclaimer, the term of this patent is extended or adjusted under 35 U.S.C. 154(b) by 1066 days.

(21) Appl. No.: 17/753,189

(22) PCT Filed: Aug. 26, 2020

(86) PCT No.: PCT/US2020/048006
§ 371 (c)(1),
(2) Date: Feb. 23, 2022

(87) PCT Pub. No.: WO2021/041548
PCT Pub. Date: Mar. 4, 2021

(65) Prior Publication Data

US 2022/0273338 A1 Sep. 1, 2022

Related U.S. Application Data

(60) Provisional application No. 62/892,457, filed on Aug. 27, 2019.

(51) Int. Cl.
*A61B 17/34* (2006.01)
*A61B 10/02* (2006.01)
(Continued)

(52) U.S. Cl.
CPC ........ *A61B 17/3403* (2013.01); *G06T 7/0012* (2013.01); *A61B 2090/376* (2016.02); *A61B 2090/3966* (2016.02)

(58) Field of Classification Search
CPC .......... A61B 17/3403; A61B 2090/376; A61B 2090/3966; A61B 10/0233;
(Continued)

(56) References Cited

U.S. PATENT DOCUMENTS 4,314,568 A * 2/1982 Loving .............. A61B 17/1322 604/116
5,389,081 A * 2/1995 Castro ................ A61B 17/3462 604/167.03

(Continued)

OTHER PUBLICATIONS

International Search Report and Written Opinion—PCT/US2020/048006—ISA/RU—Nov. 19, 2020.

*Primary Examiner* — Chelsea E Stinson
*Assistant Examiner* — Hamza A Darb
(74) *Attorney, Agent, or Firm* — Ballard Spahr LLP

(57) ABSTRACT

Various stabilizers for supporting a trocar and stylet are disclosed. In some implementations, a stabilizer may include a main portion through which a trocar and stylet may be inserted and supported, and a plurality of stabilizing portions to prevent movement of the stabilizer when the stabilizer is placed on a patient's body.

20 Claims, 5 Drawing Sheets

(51) Int. Cl.
*A61B 90/00* (2016.01)
*G06T 7/00* (2017.01)

(58) Field of Classification Search
CPC .... A61B 2017/3407; A61B 2017/3411; A61B 90/39; A61B 90/11; G06T 7/0012
See application file for complete search history.

(56) References Cited

U.S. PATENT DOCUMENTS

| | | | | |
|---|---|---|---|---|
| 6,846,218 | B2 | 1/2005 | Kermode et al. | |
| 8,057,487 | B2 | 11/2011 | Chu et al. | |
| 8,133,201 | B1 * | 3/2012 | Hurtado | A61M 5/427 604/116 |
| 8,308,715 | B2 | 11/2012 | Farnan et al. | |
| 2004/0243146 | A1 * | 12/2004 | Chesbrough | A61B 90/11 604/385.06 |
| 2005/0182464 | A1 * | 8/2005 | Schulte | A61N 1/0539 604/174 |
| 2012/0004681 | A1 * | 1/2012 | Gross | A61M 5/001 606/185 |

* cited by examiner

TROCAR AND STYLET STABILIZER

CROSS-REFERENCE TO RELATED APPLICATION

This Patent Application is a 371 national stage of PCT Application PCT/US2020/048006 filed on Aug. 26, 2020, entitled "TROCAR AND STYLET STABILIZER," which claims priority to U.S. Provisional Patent Application No. 62/892,457, filed on Aug. 27, 2019, and entitled "TROCAR AND STYLET STABILIZER," both of which are hereby expressly incorporated by reference herein.

BACKGROUND

For a patient with a suspicious lesion, such as pulmonary lesion found on a chest radiography, further information may be needed in order to properly diagnose, treat, and/or manage the lesion. The information may be obtained, for example, by obtaining a tissue specimen through radiography-guided biopsy.

DETAILED DESCRIPTION

Figure 1:
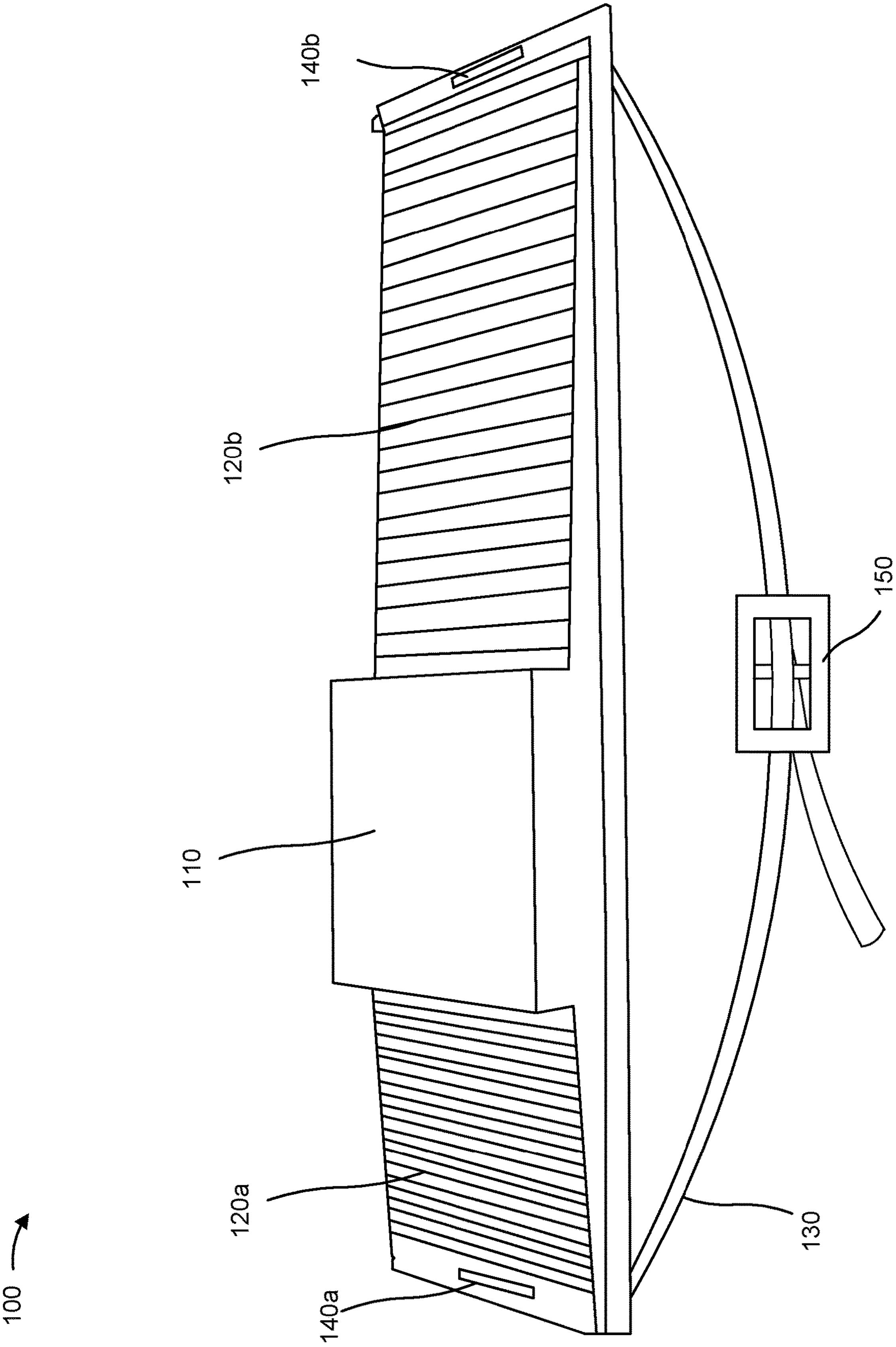
FIG. 1 is a diagram of an example stabilizer described herein.

The following detailed description of example implementations refers to the accompanying drawings. The same reference numbers in different drawings may identify the same or similar elements.

A biopsy, such as a percutaneous transthoracic biopsy, may be an outpatient procedure that is performed by a medial practitioner, such as an interventional radiologist, a diagnostic radiologist, and/or the like. During the procedure, a benzodiazepine and an opiate may be administered to the patient for minor sedation. The patient may be placed in a radiology scanner (e.g., a computed tomography (CT) scanner, an x-ray scanner, and/or the like) in a prone position or a supine position, depending on the location of the lesion. An area of the patient's skin near the lesion may be prepared in a sterile fashion, a local anesthetic may be injected, and the patient's skin may be marked for a point of entry based on imaging performed by the radiology scanner.

Once the local anesthetic has taken effect, a trocar and stylet may be introduced through the patient's skin and any organs and/or other bodily structures until the trocar and stylet are abutting the lesion. The stylet may be removed from the trocar, leaving the trocar in place. A biopsy device may be inserted through the trocar and the lesion may be sampled (e.g., a single sample or a plurality of samples, such as three to five samples, may be obtained). Once the samples have been recovered, the biopsy device may be removed from the trocar and the stylet may be reintroduced back into the trocar so that the stylet and the trocar may be removed from the patient. Once the stylet and the trocar are removed from the patient, a small bandage may be placed on the entry point of the trocar and stylet, and the patient may be monitored (e.g., up to 4 hours or more) with serial radiological imaging for a determination of pneumothorax.

As the medical practitioner advances the trocar and stylet to the patient's body, radiological images may be taken to ensure that the trocar and stylet are on a proper trajectory to sample the lesion. However, due to the length of the trocar and stylet, and the weight distribution of the trocar and stylet (i.e., the majority of the weight of the trocar and stylet being located near the handle of the trocar and stylet), the trocar and stylet may need to be inserted far enough into the patient's body so that the patient's body may stabilize the trocar and stylet for radiological imaging. If the trocar and stylet are not supported during radiological imaging, the lack of stabilization may compromise image quality, the trocar and stylet may become dislodged from the patient's body, and/or the like. The medical practitioner may attempt to use towels or rolled-up sheets to support the trocar and stylet, but such techniques may be cumbersome and result in improper alignment of the trocar and stylet relative to the lesion.

Some implementations, described herein, provide a stabilizer for use with a trocar and stylet. The stabilizer may act as an external support to allow a medical practitioner to stabilize and align the trocar and stylet ex-vivo. In this way, the stabilizer reduces the amount of readjustments (e.g., to the trocar and stylet) that are needed in order to ensure that the trocar and stylet are inserted into a patient at a desired trajectory. This reduces the quantity of pleural crossings that may occur due to readjustment of the trocar and stylet, which in turn may reduce the overall incidence of pneumothorax and/or other medical injuries. Moreover, since the stabilizer reduces the amount trocar and stylet readjustments, the quantity of radiological images that are captured after each readjustment is reduced, which in turn reduces the amount of radiation exposure for a patient as well as the medical practitioner performing the radiological imaging.

FIG. 1 is a diagram of an example stabilizer 100 for use with a trocar and stylet. As shown in FIG. 1, stabilizer 100 may include a main portion 110 and a set of stabilizing portions **120*a* and 120*b*, a strap 130, a set of strap attachments 140*a* and 140*b*, and a strap adjuster 150. Main portion 110 (which may be referred to herein as a "trocar and stylet receiving portion") may be a portion of stabilizer 100 through with a trocar and stylet may be inserted in order to provide ex-vivo support for the trocar and stylet. Main portion 110 may be of various sizes, shapes, and/or materials. The thickness of main portion 110** may be sized to support trocars and stylets of various sizes and/or weights.

In some implementations, main portion 110 may be constructed from a translucent material such that a medical practitioner may view a portion of a patient's body through main portion 110 in order to properly align the trocar and stylet to an entry point in the patient's body. The translucent material may be selected such that main portion 110 is capable of supporting the weight of various sizes and/or shapes of trocars and stylets. In some implementations, the material of main portion 110 may be selected from a silicone, rubber, cellulose, hydrogel, polyvinyl alcohol (PVA), polytetrafluoroethylene (PTFE), polyurethane, thermoplastic elastomer, thermoplastic rubber, and/or other gel or elastomeric based materials. The material may be a singular material or a combination of at least one of the materials above. As an example, the material may include a clear silicone rubber.

In some implementations, the combinations and/or compositions of materials may include various percentages (e.g., by weight, by volume, or the like) of materials included therein. For example, the combination may include a first percentage of a first material component, a second percentage of a second material component, and so on, and/or the like. The percentages of material components included therein may be the same percentage, may be different percentages, and/or the like. As an example, the first material component may be from 1% to 99% of the combination and the second material component may be 1% to 99% of the combination. As another example, the first material component may be from 0.1% to 99.9% of the combination and the second material component may be 0.1% to 99.9% of the combination. As another example, the first material component may be from 0.01% to 99.99% of the combination and the second material component may be 0.01% to 99.99% of the combination. As another example, the first material component may be greater than 0% and less than 100% of the combination and the second material component may be greater than 0% and less than 100% of the combination.

In some implementations, the material may have various ranges of physical and/or chemical properties. As an example, the material may have a Shore 00 hardness range (e.g., for rubbers that are harder and/or firmer) of about 0 to 80, of about 0 to 50, and/or the like. As another example, the material may have a Shore A hardness range (e.g., for materials such as gels and soft rubbers) of about 0 to 40. As another example, the material may have a tensile strength range of about 50 to 350 pounds per square inch (psi), of about 75 to 325 psi, of about 100 to 300 psi, of about 125 to 275 psi, of about 150 to 250 psi, and/or the like. As another example, the material may have a Shore A hardness of 15 and a tensile strength of 180 psi. In some implementations, the material of main portion 110 may be selected such that the trocar and stylet may be inserted through main portion 110.

In some implementations, the material of main portion 110 may be selected such that a scalpel or other sharp device may be used to cut form openings in main portion 110. In some implementations, radiopaque markings (e.g., crosshatchings or other patterns) may be printed, etched, and/or suspended within the material of main portion 110 to assist the medical practitioner in properly aligning the trocar and stylet with the entry point in the patient's body.

Stabilizing portions 120*a* and 120*b* may include elongated wings, flaps, and/or other structural members that stabilize stabilizer 100 when rested on a patient's body. That is, stabilizing portions 120*a* and 120*b* may be shaped, molded (e.g., to the patient's body), and/or configured to prevent stabilizer 100 from inadvertently or accidently moving or sliding when rested on a patient's body. In this way, stabilizing portions 120*a* and 120*b* may aid the medical practitioner in properly aligning the trocar and stylet with the entry point in the patient's body.

In some implementations, stabilizing portions 120*a* and 120*b* may be the same thickness as main portion 110. In some implementations, stabilizing portions 120*a* and 120*b* may be a different thickness than main portion 110. Moreover, stabilizing portions 120*a* and 120*b* may be tapered from main portion 110 to respective opposite ends of stabilizing portions 120*a* and 120*b* such that the weight of stabilizer 100 is distributed more toward main portion 110.

Stabilizing portions 120*a* and 120*b* may be constructed using various materials. In some implementations, stabilizing portions 120*a* and 120*b* may be constructed of a flexible and/or malleable material (e.g., a silicone and/or rubber material) such that stabilizer 100 is capable of conforming to the contours of the patient's body, which provides increased stability of stabilizer 100. Moreover, to further increase stability of stabilizer 100, small ridges or grooves may be formed on an underside of stabilizing portions 120*a* and 120*b* to increase friction (and thus resistance to movement) of stabilizing portions 120*a* and 120*b*. In addition, to further increase stability of stabilizer 100, the underside of stabilizer 100 may be coated with an adhesive backing, which may permit stabilizer 100 to be removably adhered to the patient's body. The adhesive backing may further provide an air seal around the point of entry of the trocar and stylet, which may prevent external air and/or liquid from entering into the patient's body and causing complications such as pneumothorax (e.g., a collection of air within a pleural space) and/or pleural effusion (e.g., a fluid accumulation within a pleural space). In some implementations, the adhesive backing may be included on at least a portion of the underside of main portion 110 and/or at least a portion of stabilizing portions 120*a* and 120*b*.

In some implementations, stabilizing portions 120*a* and/or 120*b* may be removable from main portion 110. For example, stabilizer 100 may be constructed such that respective perforated sections or lines between main portion 110 and stabilizing portions 120*a* and/or 120*b* are formed, which permit stabilizing portions 120*a* and/or 120*b* to be removed from main portion 110 (e.g., by tearing or pulling stabilizing portions 120*a* and/or 120*b* off from main portion 110 at the respective perforated sections). In some implementations, stabilizing portions 120*a* and/or 120*b* may include respective sets of one or more perforated sections or lines such that the size of stabilizing portions 120*a* and/or 120*b* can be adjusted by removing sub-portions from stabilizing portions 120*a* and/or 120*b*.

In some implementations, stabilizing portions 120*a* and 120*b* may be sized and/or shaped such that stabilizer 100 may be used with patients of various sizes and/or used for various types of procedures. In some implementations, stabilizing portions 120*a* and 120*b* may be the same size. In some implementations, stabilizing portions 120*a* and 120*b* may be different sizes to provide stabilization for positioning of stabilizer 100 at various locations on the patient's body. For example, and as shown in FIG. 1, stabilizing portion 120*b* may be longer relative to stabilizing portion 120*a*, which may permit main portion 110 to be positioned over a lung of the patient for a biopsy procedure to sample a lesion in the lung.

Additionally, or alternatively, strap 130 may be attached to stabilizing portions 120*a* and 120*b* via strap attachments 140*a* and 140*b*, respectively. Strap 130 is configured to maintain a position of stabilizer 100 relative to a patient's body by being attached to stabilizer 100 (e.g., based on being wrapped around a portion of the patient's body or attached to a support structure associated with the patient). Strap 130 may be formed from any suitable material. For example, strap 130 may be formed from stretchable fibers (e.g., to allow for flexibility to fit to a patient's body shape) and/or non-stretchable fibers (e.g., that provide added strength and/or prevent movement relative to the patient's body or other support structure). Strap 130 may be formed from two separate straps (e.g., a first strap attached to stabilizing portion 120*a* via strap attachment 140*a* and a second strap attached to stabilizing portion 120*b* via strap attachment 140*b*). As shown in FIG. 1, the two separate straps may be attached together via strap adjuster 150 to form strap 130. In some implementations, strap 130 may include a single strap with a length between strap attachments 140*a* and 140*b* via adjustment mechanisms associated with strap attachments 140*a* and 140*b*. For example, strap adjuster 150 may be movable toward and/or may be situated at (and/or combined with) one or both of strap attachments 140*a* and 140*b* (e.g., according to a position of the patient and/or to improve comfort of the patient).

A length of strap 130 between strap attachments 140*a* and 140*b* may include any suitable mechanism that permits strap 130 to be attached to stabilizing portions 120*a* and 120*b*. For example, the strap attachments 140*a* and 140*b* may include a fastener mechanism that permits the strap 130 to be fastened to the be adjusted via strap adjuster 150. The strap attachments 140*a* and 140*b* are configured to permit strap 130 to be attached to the strap adjuster 150 may include any type of strap connecting mechanism, such as a buckle, fastener, clip, loop, and/or the like. Additionally, or alternatively, strap 130 may include a self-adhesive mechanism (e.g., a hook and loop fastener, a glue, and/or the like) to permit one or more ends of strap 130 to be looped through strap attachments 140*a* and 140*b* (and/or strap adjuster 150) and reattached to another portion of strap 130 via the self-adhesive mechanism.

Although FIG. 1 and some examples described herein describe strap 130 being wrapped around a patient and/or attached at strap attachments 140*a* and 140*b*, other configurations of one or more straps (or other mechanisms to stabilize stabilizer 100) are possible. For example, one or more straps may be configured to attach to stabilizer 100 (e.g., via strap attachments 140*a* and 140*b*) and to another structure (e.g., a structure supporting the patient, such as a bed, platform of an imaging device, and/or the like). In such a case, stabilizer 100 may be stabilized relative to both the patient and/or the structure.

As indicated above, FIG. 1 is provided merely as an example. Other examples may differ from what is described with regard to FIG. 1.

Figure 2:
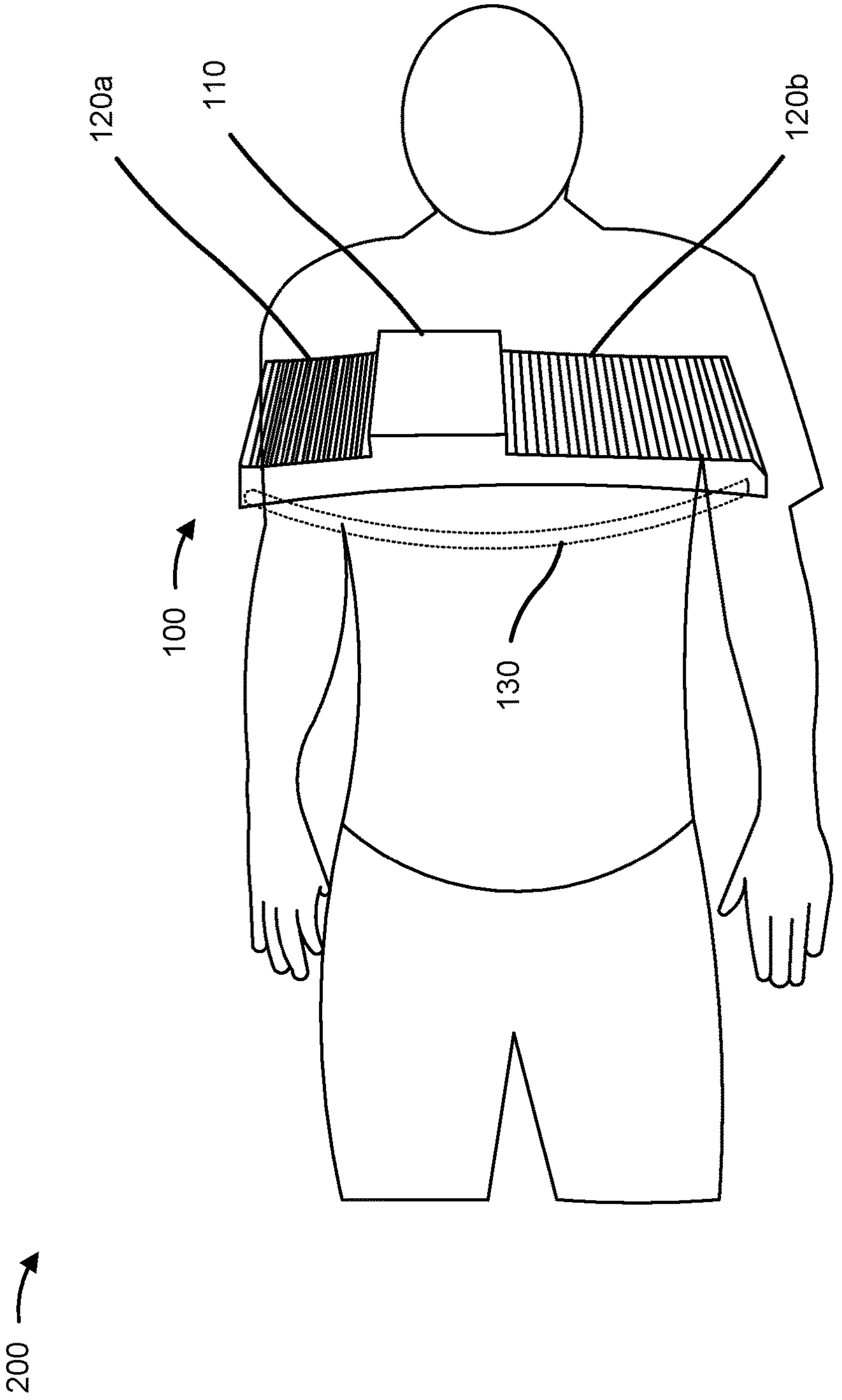
FIG. 2 is a diagram of an example implementation of the example stabilizer of FIG. 1.

FIG. 2 is a diagram of an example implementation 200 of stabilizer 100. As shown in FIG. 2, stabilizer 100 may be placed across a patient's body such that main portion 110 is located over an entry point in the patient's body. As further shown in FIG. 2, stabilizing portions 120*a* and 120*b* may conform to the contours of the patient's body to provide stability for stabilizer 100. Additionally, or alternatively, strap 130 may conform to the contours of the patient's body. In example implementation 200 illustrated in FIG. 2, main portion 110 may be located over a point of entry in the patient's right lung such that a biopsy may be sampled from a lesion in the patient's right lung. In this case, the relatively longer stabilizing portion 120*b* may be positioned such that stabilizing portion 120*b* rests across a larger portion of the patient's chest than stabilizing portion 120*a*.

As indicated above, FIG. 2 is provided merely as an example. Other examples may differ from what is described with regard to FIG. 2.

Figure 3:
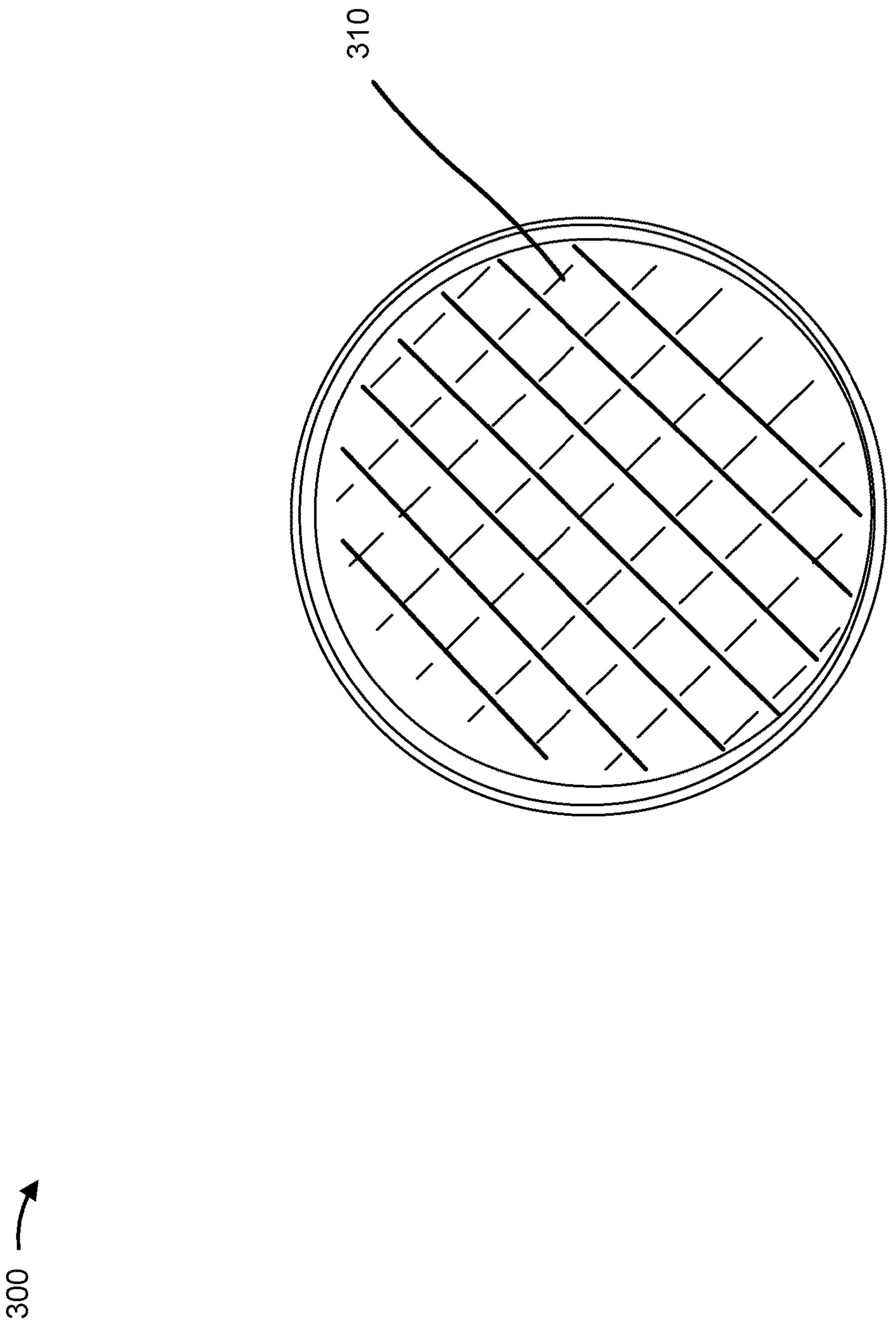
FIG. 3 is a diagram of an example stabilizer described herein.

FIG. 3 is a diagram of an example stabilizer 300 for use with a trocar and stylet. Stabilizer 300 may be a compact version of stabilizer 100 of FIG. 1, such that stabilizer 300 may be used at locations on a patient's body that offer less working space for the medical practitioner. As shown in FIG. 3, stabilizer 300 may be composed entirely of a main portion without a set of stabilizing portions. The size, shape, and/or material of stabilizer 300 may be similar to main portion 110 of stabilizer 100. As further shown in FIG. 3, stabilizer 300 may include a set of radiopaque markings 310 (e.g., cross-hatchings or other patterns) that may be printed, etched, and/or suspended within the material of stabilizer 300 to assist the medical practitioner in properly aligning the trocar and stylet with the entry point in the patient's body.

As indicated above, FIG. 3 is provided merely as an example. Other examples may differ from what was described with regard to FIG. 3.

Figure 4:
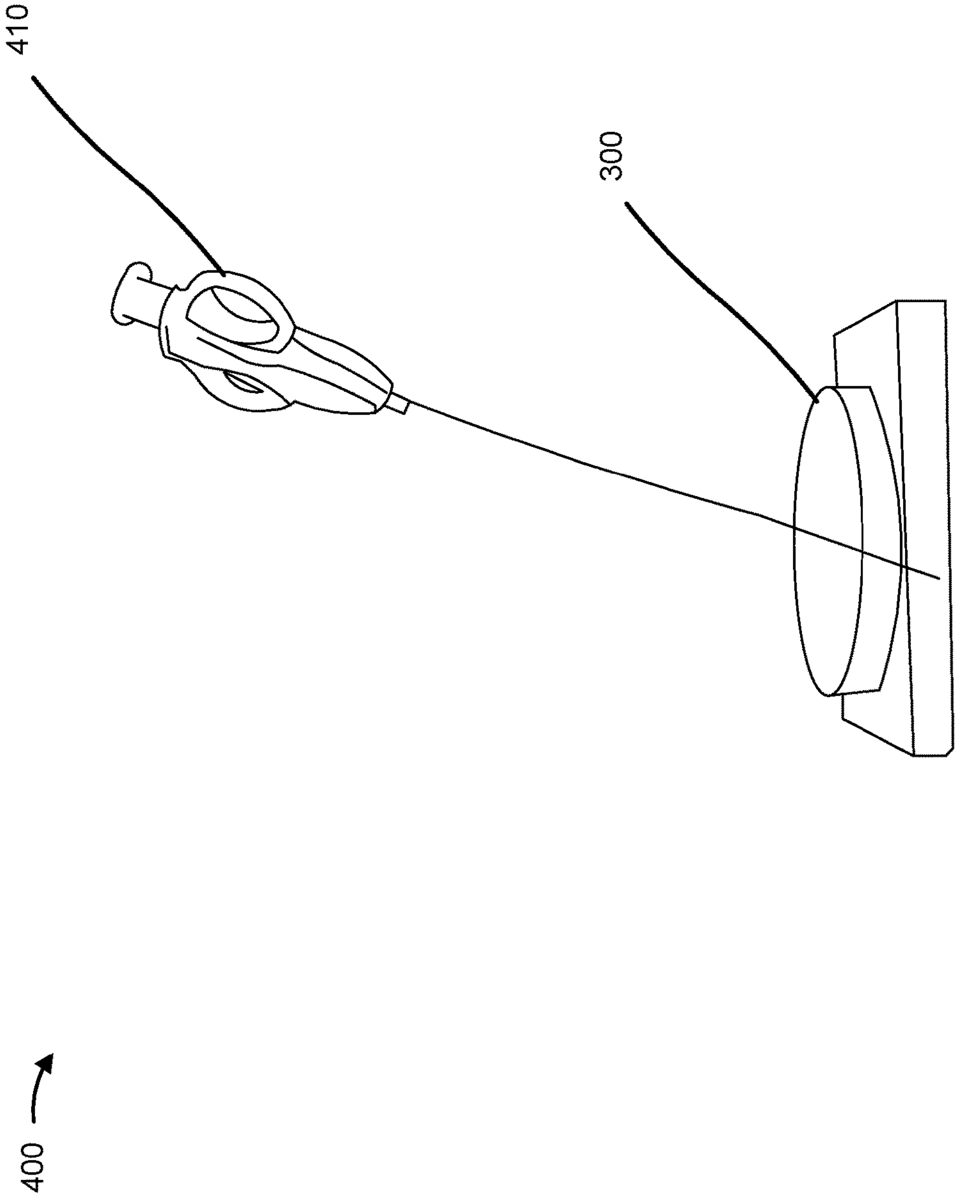
FIG. 4 is a diagram of an example implementation of the example stabilizer of FIG. 3.

FIG. 4 is a diagram of an example implementation 400 of stabilizer 300. As shown in FIG. 4, stabilizer 300 may support a trocar 410 and stylet (e.g., which may be inserted into trocar 410) when trocar 410 is inserted into stabilizer 300. In this way, a radiological image of trocar 410 and the stylet, inserted into a body of a patient, may be captured during a procedure, such as a biopsy procedure.

As indicated above, FIG. 4 is provided merely as an example. Other examples may differ from what is described with regard to FIG. 4.

Figure 5:
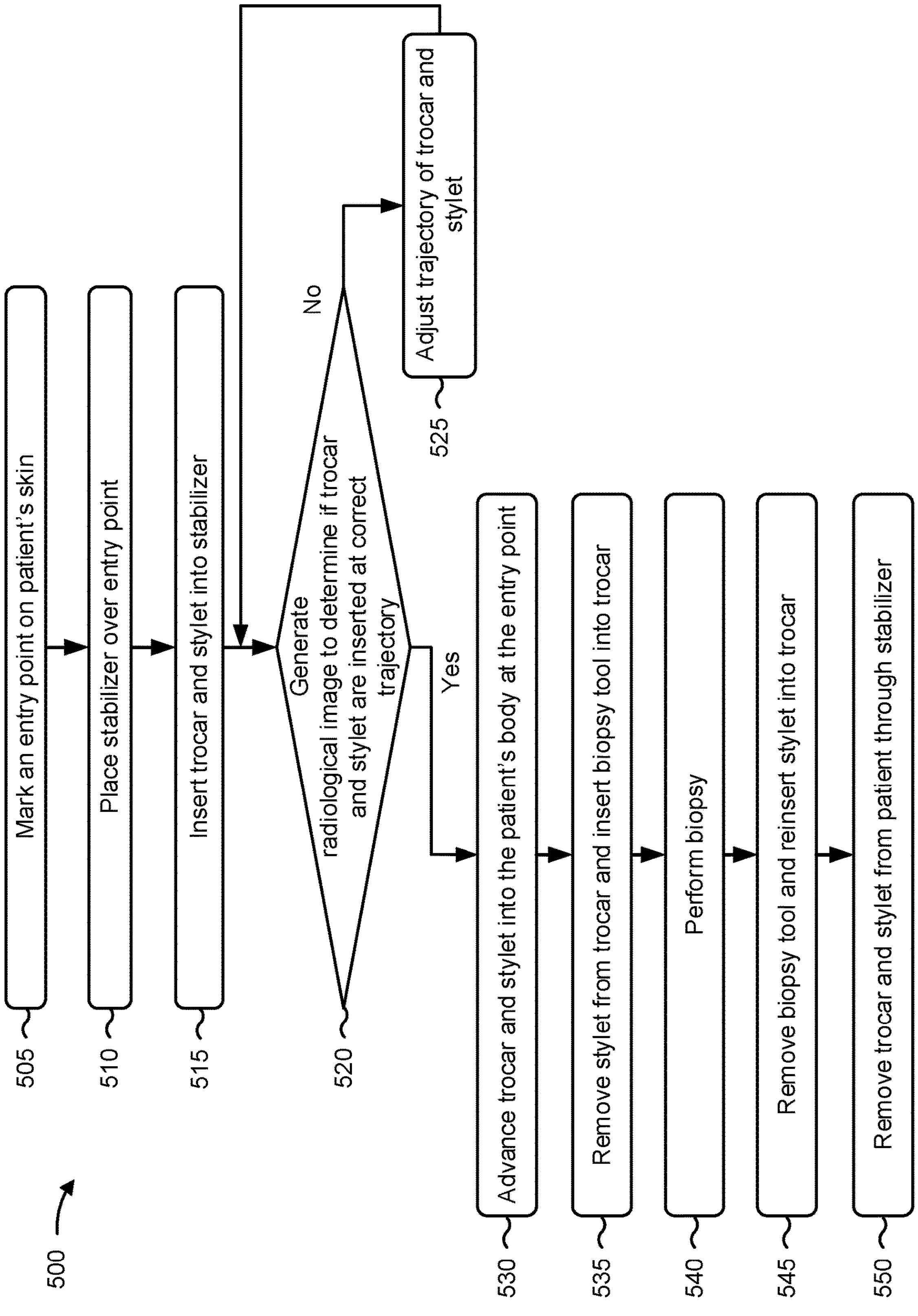
FIG. 5 is a flow chart of an example process for a medical procedure using a stabilizer.

FIG. 5 is a flow chart of an example process 500 for a medical procedure using a stabilizer. In some implementations, one or more process blocks of FIG. 5 may include the use of a stabilizer, such as stabilizer 100, stabilizer 300, and/or the like. In some implementations, one or more process blocks of FIG. 5 may include the use of another device or a group of devices separate from or including the stabilizer.

As shown in FIG. 5, process 500 may include marking an entry point on a patient's skin (block 505). The entry point may include an entry point, in the patient's body, for a trocar and stylet. In some implementations, the location of the entry point may be based on a location of a lesion from which a biopsy sample is to be obtained in the medical procedure. The lesion may include, for example, a lesion in a thyroid, a lung, a kidney, a liver, a lymph node, a mediastinum, and/or the like. In some implementations, the location of the entry point may be based on a location where a percutaneous ablation of tissue is to occur. In some implementations, the location of the entry point may be based on an abscess that is to be drained. In some implementations, the mark may include a skin nick made with a scalpel or another medical device, may include a mark made by a marking or another drawing device, may include a laser marking made by a laser device, and/or the like.

As further shown in FIG. 5, process 500 may placing a stabilizer over the entry point (block 510). For example, the stabilizer may be placed over the entry point such that a main portion of the stabilizer (e.g., a portion of the stabilizer through which the trocar and stylet are to be inserted) is located over the entry point. In some implementations, the stabilizer may be placed such that stabilizing portions, of the stabilizer, are positioned to prevent the stabilizer from moving during the medical procedure. In some implementations, if the stabilizer includes an adhesive backing, the stabilizer may be pressed against the patient's body in order to ensure proper temporary bonding of the adhesive to the patient's skin to provide further stability of the stabilizer. In some implementations, a medical practitioner may place the stabilizer over the entry point. In some implementations, a device (e.g., a robotic arm, a processor, a memory device, and/or another device) may automatically place the stabilizer over the entry point. For example, the device may use computer vision to identify the entry point and place the stabilizer over the entry point.

As further shown in FIG. 5, process 500 may include inserting the trocar and stylet into the stabilizer (block 515). In some implementations, the trocar and stylet may be partially inserted into the stabilizer. In some implementations, the trocar and stylet may be fully inserted into the stabilizer. In some implementations, a medical practitioner may insert the trocar and stylet using radiological markings that are included on the stabilizer. In some implementations, a device (e.g., a robotic arm, a processor, a memory device, and/or another device) may automatically insert the trocar and stylet. For example, the device may use computer vision to identify the entry point and insert the trocar and stylet.

As further shown in FIG. 5, process 500 may include generating a radiological image to determine if the trocar and stylet are inserted, into the stabilizer, a correct trajectory (block 520). In some implementations, the radiological image may include a CT scan, an X-ray, and/or another type of radiological image. In some implementations, a medical practitioner may determine whether trajectory of the trocar and stylet is such that the trocar and stylet is aligned with the entry point and/or the lesion based on the radiological image. In some implementations, a device (e.g., a processor, a memory device, and/or another device) may automatically cause a radiological scanner (e.g., a CT scanner, an X-ray scanner, and/or the like) to capture the radiological image and/or may automatically determine whether trajectory of the trocar and stylet is such that the trocar and stylet is aligned with the entry point and/or lesion. For example, the device may use various computer vision techniques to determine whether trajectory of the trocar and stylet is such that the trocar and stylet is aligned with the entry point and/or lesion.

As further shown in FIG. 5, if the trocar and stylet are not inserted at the correct trajectory (block 520—No), process 500 may include adjusting the trajectory of the trocar and stylet (block 525). In some implementations, a medical practitioner may adjust the trajectory of the trocar and stylet by partially or fully removing the trocar and stylet from the stabilizer and reinserting and advancing the trocar and stylet into the stabilizer at another trajectory. In some implementations, a device (e.g., a robotic arm, a processor, a memory device, and/or another device) may automatically adjust the trajectory of the trocar and stylet by partially or fully removing the trocar and stylet from the stabilizer and reinserting and advancing the trocar and stylet into the stabilizer at another trajectory. In some implementations, once the trajectory of the trocar and stylet has been adjusted, process 500 may return to block 520, where another radiological image may be generated to determine if the trocar and stylet are inserted at the correct trajectory.

As further shown in FIG. 5, if the trocar and stylet are inserted at the correct trajectory (block 520—Yes), process 500 may include advancing the trocar and stylet into the patient's body at the entry point (block 530). In some implementations, the trocar and stylet may be inserted through a chest wall and/or other body organs of the patient such that a tip of the trocar and stylet is placed in or near the lesion. In some implementations, a device (e.g., a robotic arm, a processor, a memory device, and/or another device) may advance the trocar and stylet into the patient's body at the entry point.

As further shown in FIG. 5, process 500 may include removing the stylet from the trocar and inserting a biopsy tool into the trocar (block 535). In some implementations, the biopsy tool may include a biopsy gun, a biopsy needle, and/or another type of biopsy tool that is capable of obtaining a biopsy sample from the lesion. In some implementations, a medical practitioner may remove the stylet from the trocar and inserting a biopsy tool into the trocar. In some implementations, a device (e.g., a robotic arm, a processor, a memory device, and/or another device) may automatically remove the stylet from the trocar and inserting a biopsy tool into the trocar.

As further shown in FIG. 5, process 500 may include performing a biopsy of the lesion (block 540). For example, the biopsy tool may be used to obtain a biopsy sample from the lesion. In some implementations, a plurality of biopsy samples may be obtained from the lesion using the biopsy tool. In some implementations, a medical practitioner may use the biopsy tool to obtain the biopsy sample. In some implementations, a device (e.g., a robotic arm, a processor, a memory device, and/or another device) may automatically control the biopsy tool to obtain the biopsy sample.

As further shown in FIG. 5, process 500 may include removing the biopsy tool from the trocar and reinserting the stylet into the trocar (block 545). As further shown in FIG. 5, process 500 may include removing the trocar and stylet from the patient through the stabilizer (block 550). In some implementations, a medical practitioner may remove the biopsy tool from the trocar and reinsert the stylet into the trocar. In some implementations, a device (e.g., a robotic arm, a processor, a memory device, and/or another device) may automatically remove the biopsy tool from the trocar and reinsert the stylet into the trocar.

Process 500 may include additional implementations, such as any single implementation or any combination of implementations described below and/or described with regard to any other process described herein.

In some implementations, the stabilizer may include an adhesive backing on an underside of the stabilizer, and process 500 may include temporarily bonding, using the adhesive backing, the stabilizer to the patient's skin. In some implementations, the radiological image comprises includes a CT scan or an X-ray scan. In some implementations, process 500 may include determining that the trocar and the stylet are not inserted at the correct trajectory, adjusting a trajectory of the trocar and the stylet based on determining that the trocar and the stylet are not inserted at the correct trajectory, and generating another radiological image based on adjusting the trajectory of the trocar and the stylet.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

The foregoing disclosure provides illustration and description, but is not intended to be exhaustive or to limit the implementations to the precise form disclosed. Modifications and variations may be made in light of the above disclosure or may be acquired from practice of the implementations.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A method, comprising:
placing a stabilizer over an entry point in a patient's body;
inserting a trocar and a stylet into the stabilizer,
wherein the stabilizer comprises:
a main portion through which the trocar and the stylet is inserted; and
a plurality of stabilizing portions of the stabilizer,
wherein the plurality of stabilizing portions are configured to be removable from the main portion based on at least one of perforated sections or lines between the main portion and the plurality of stabilizing portions, and
wherein the at least one of the perforated sections or the lines are configured to enable adjustment of a size of the plurality of stabilizing portions by removing a subset of the plurality of stabilizing portions;
generating a radiological image to determine if the trocar and the stylet are inserted at a correct trajectory;
advancing the trocar and the stylet into the patient's body at the entry point based on determining that the trocar and the stylet are inserted at the correct trajectory;
removing the stylet from the trocar based on advancing the trocar and the stylet into the patient's body;
inserting a biopsy tool into the trocar;
performing a biopsy using the biopsy tool;
removing the biopsy tool from the trocar and reinserting the stylet into the trocar; and
removing the trocar and the stylet from the patient's body through the stabilizer.

2. The method of claim 1, wherein the stabilizer comprises:
an adhesive backing on an underside of the stabilizer; and
wherein the method further comprises:
temporarily bonding, using the adhesive backing, the stabilizer to skin of the patient's body.

3. The method of claim 1, wherein the radiological image comprises:
a computed tomography (CT) scan, or
an X-ray scan.

4. The method of claim 1, further comprising:
determining that the trocar and the stylet are not inserted at the correct trajectory;
adjusting a trajectory of the trocar and the stylet based on determining that the trocar and the stylet are not inserted at the correct trajectory; and
generating another radiological image based on adjusting the trajectory of the trocar and the stylet.

5. The method of claim 1, wherein the stabilizer comprises of a translucent material.

6. The method of claim 1, wherein the stabilizer comprises of a translucent material, and
wherein the translucent material comprises a combination of a first material and a second material.

7. The method of claim 1, wherein the main portion comprises a plurality of radiopaque markings to assist in guiding the trocar and the stylet.

8. A system, comprising:
a trocar;
a stylet; and
a stabilizer,
wherein the stabilizer is placed over an entry point in a patient's body;
wherein the trocar and the stylet are inserted into the stabilizer,
wherein the stabilizer comprises:
a main portion through which the trocar and the stylet is inserted, and
a plurality of stabilizing portions of the stabilizer,
wherein the plurality of stabilizing portions are configured to be removable from the main portion based on at least one of perforated sections or lines between the main portion and the plurality of stabilizing portions, and
wherein the at least one of the perforated sections or the lines are configured to enable adjustment of a size of the plurality of stabilizing portions by removing a subset of the plurality of stabilizing portions,
wherein the system is configured to be used with a biopsy procedure, wherein the biopsy procedure comprises a radiological image that is generated to determine if the trocar and the stylet are inserted at a correct trajectory,
wherein the trocar and the stylet are advanced into the patient's body at the entry point based on determining that the trocar and the stylet are inserted at the correct trajectory,
wherein the stylet is removed from the trocar based on advancing the trocar and the stylet into the patient's body,
wherein a biopsy tool is inserted into the trocar,
wherein a biopsy is performed using the biopsy tool,
wherein the biopsy tool is removed from the trocar and reinserting the stylet into the trocar; and
wherein the trocar and the stylet are removed from the patient's body through the stabilizer.

9. The system of claim 8, wherein the stabilizer comprises:
an adhesive backing on an underside of the stabilizer,
wherein the stabilizer is temporarily bonded to skin of the patient's body, using the adhesive backing.

10. The system of claim 8, wherein the radiological image comprises:
a computed tomography (CT) scan, or
an X-ray scan.

11. The system of claim 8, wherein the trocar and the stylet are determined as not being inserted at the correct trajectory,
wherein a trajectory of the trocar and the stylet are adjusted based on determining that the trocar and the stylet are not inserted at the correct trajectory; and
wherein another radiological image is generated based on adjusting the trajectory of the trocar and the stylet.

12. The system of claim 8, wherein the stabilizer comprises of a translucent material.

13. The system of claim 8, wherein the stabilizer comprises of a translucent material, and
wherein the translucent material comprises a combination of a first material and a second material.

14. The system of claim 8, wherein the main portion comprises a plurality of radiopaque markings to assist in guiding the trocar and the stylet.

15. The system of claim 8, wherein the stabilizer comprises of a translucent material, and
wherein the translucent material comprises a combination of a first material and a second material.

16. A device, comprising:
a stabilizer, wherein the stabilizer is placed over an entry point in a patient's body;

wherein a trocar and a stylet are inserted into the stabilizer, wherein the stabilizer comprises:

a main portion through which the trocar and the stylet is inserted, and a plurality of stabilizing portions of the stabilizer, wherein the plurality of stabilizing portions are configured to be removable from the main portion based on at least one of perforated sections or lines between the main portion and the plurality of stabilizing portions, and wherein the at least one of the perforated sections or the lines are configured to enable adjustment of a size of the plurality of stabilizing portions by removing a subset of the plurality of stabilizing portions, wherein the device is configured to be used with a biopsy procedure, wherein the biopsy procedure comprises a radiological image that is generated to determine if the trocar and the stylet are inserted at a correct trajectory, wherein the trocar and the stylet are advanced into the patient's body at the entry point based on determining that the trocar and the stylet are inserted at the correct trajectory, wherein the stylet is removed from the trocar based on advancing the trocar and the stylet into the patient's body, wherein a biopsy tool is inserted into the trocar, wherein a biopsy is performed using the biopsy tool, wherein the biopsy tool is removed from the trocar and reinserting the stylet into the trocar; and wherein the trocar and the stylet are removed from the patient's body through the stabilizer.

17. The device of claim 16, wherein the stabilizer comprises:

an adhesive backing on an underside of the stabilizer, wherein the stabilizer is temporarily bonded to skin of the patient's body, using the adhesive backing.

18. The device of claim 16, wherein the radiological image comprises:

a computed tomography (CT) scan, or an X-ray scan.

19. The device of claim 16, wherein the trocar and the stylet are determined as not being inserted at the correct trajectory, wherein a trajectory of the trocar and the stylet are adjusted based on determining that the trocar and the stylet are not inserted at the correct trajectory; and wherein another radiological image is generated based on adjusting the trajectory of the trocar and the stylet.

20. The device of claim 16, wherein the stabilizer comprises of a translucent material.

* * * * *